United States Patent
Haller et al.

(10) Patent No.: US 10,433,951 B2
(45) Date of Patent: Oct. 8, 2019

(54) DEPTH OF FOCUS AND VISUAL ACUITY USING COLORIZED APODIZATION OF INTRA-OCULAR LENSES

(71) Applicant: RxSight, Inc., Aliso Viejo, CA (US)

(72) Inventors: Matt Haller, Costa Mesa, CA (US); Christian A. Sandstedt, Pasadena, CA (US); Robert H. Grubbs, South Pasadena, CA (US)

(73) Assignee: RxSight, Inc., Aliso Viejo, CA (US)

( * ) Notice: Subject to any disclaimer, the term of this patent is extended or adjusted under 35 U.S.C. 154(b) by 0 days.

(21) Appl. No.: 15/600,792

(22) Filed: May 22, 2017

(65) Prior Publication Data

US 2018/0333256 A1 Nov. 22, 2018

(51) Int. Cl.
    *A61F 2/16* (2006.01)
(52) U.S. Cl.
    CPC .......... *A61F 2/1659* (2013.01); *A61F 2/1624* (2013.01); *A61F 2002/1681* (2013.01); *A61F 2002/16965* (2015.04)
(58) Field of Classification Search
    CPC ........ A61F 2/1659; A61F 2/1624; A61F 2/16; A61F 2/1613; A61F 2002/16965; A61F 2002/1681; A61F 2002/1696
    See application file for complete search history.

(56) References Cited

U.S. PATENT DOCUMENTS

| | | | |
|---|---|---|---|
| 6,450,642 B1 | 9/2002 | Jethmalani et al. | |
| 7,341,599 B1 | 3/2008 | Peyman | |
| 8,343,215 B2 | 1/2013 | Miller et al. | |
| 8,500,805 B2 * | 8/2013 | Kobayashi | A61F 2/1618 351/159.11 |
| 9,119,710 B2 | 9/2015 | Grubbs et al. | |
| 2007/0216861 A1 | 9/2007 | Ishak et al. | |

(Continued)

OTHER PUBLICATIONS

Nicholas Tarantino, O.D., "AcuFocus KAMRA™ Inlay," United States Food and Drug Administration Opthalmic Devices Advisory Committee, Jun. 6, 2014, pp. 1-185.

(Continued)

*Primary Examiner* — David H Willse
*Assistant Examiner* — Tiffany P Shipmon

(57) ABSTRACT

A color-apodized intraocular lens includes a lens center, with a center-transmittance to transmit an incident light; a lens annul us, surrounding the lens center, configured to selectively attenuate the incident light according to a radius- and wavelength-dependent annulus-transmittance, wherein the annulus-transmittance is less than the center-transmittance, in a short wavelength spectral range; and haptics, extending from the lens annulus. A method of making a color-apodized intraocular lens includes creating an intraocular lens mold using a base-polymer, the intraocular lens having a lens center, with a center-transmittance to transmit an incident light; a lens annulus, surrounding the lens center, configured to selectively attenuate the incident light according to a radius and wavelength-dependent annulus-transmittance, wherein the annulus-transmittance is less than the center-transmittance in a short wavelength spectral range; forming haptics, extending from the lens annulus; and applying a stimulus to the intraocular lens mold to form the color-apodized intraocular lens.

14 Claims, 11 Drawing Sheets

(56) References Cited

U.S. PATENT DOCUMENTS

| | | | |
|---|---|---|---|
| 2010/0103371 A1* | 4/2010 | Sarver | G02B 5/1876 351/159.01 |
| 2011/0098811 A1 | 4/2011 | Hong et al. | |
| 2014/0268034 A1 | 9/2014 | Wooley et al. | |
| 2016/0339657 A1* | 11/2016 | Grubbs | B29D 11/00461 |

OTHER PUBLICATIONS

Fernández, et al. "Impact on stereo-acuity of two presbyopia correction approaches: monovision and small aperture inlay," Biomed Opt Express, May 8, 2013, vol. 4, No. 6, 822-830.

AcuFocus™, Inc., "KAMRA® Inlay—Model ACI 7000—6.0 Summary of Safety and Effectiveness Data," pp. 1-32, Irvine.

AcuFocus, Inc., "KAMRA® Inlay—Professional Use Information," pp. 1-46, Irvine.

Andrew Kay, et al., "Extended depth of field by colored apodization," Optics Letters, Dec. 1, 2011, vol. 36, No. 23.

Enrique J. Fernandez and Pablo Artal, "Achromatic doublet intraocular lens for full aberration correction," Biomedical Optics Express 23, May 1, 2017, vol. 8, No. 5, pp. 1-9.

Gross et al., "Human eye," Handbook of Optical Systems: vol. 4 Survey of Optical Instruments. Edited by Herbert Gross, Mar. 2008, pp. 1-87.

D. A. Atchison and H. Guo, "Subjective Blur Limits for Higher Order Aberrations," Optometry and Vision Science, vol. 87, No. 11, Nov. 2010, pp. E890-E898.

Kay et al., "Extended depth of field by colored apodization," Optics Letters, vol. 36, No. 23, Dec. 1, 2011, pp. 4614-4616.

Atchison et al., "Limits of spherical blur determined with an adaptive optics mirror," Ophtha. Physio. Opt., vol. 29, No. 3, 2009, pp. 300-311.

J. C. Wyant and K. Creath, "Basic Wavefront Aberration Theory for Optical Metrology," Applied Optics and Optical Engineering, vol. XI, 1992, pp. 1-12.

* cited by examiner

DEPTH OF FOCUS AND VISUAL ACUITY USING COLORIZED APODIZATION OF INTRA-OCULAR LENSES

TECHNICAL FIELD

This invention relates to intra-ocular lenses, and more specifically to intraocular lenses with a colorized apodization to offer improvements in visual acuity for presbyopia patients,

BACKGROUND

FIGS. 1A-D illustrate the problem of presbyopia. FIGS. 1A-B illustrate that a non-presbyopic eye 1 can image both a distant object and a nearby object to the retina 3 by changing the shape of a crystalline lens 5. FIGS. 1C-D illustrate that a presbyopic eye 1 loses its ability to image nearby objects to the retina 3, because the flexibility of the crystalline lens 5 is diminished by the advancing age of the patients. When looking at a nearby object, the crystalline lens 5 cannot accommodate and change its shape to a sufficient degree, and the object gets imaged behind the retina.

Presbyopia is often alleviated by prescribing bifocal, multifocal, and progressive lenses that focus some light at a primary focus and then distribute the remaining light to one or more other foci. These lens designs can be employed in eye glasses, in contact lenses, and in intraocular lenses (IOLs), inserted into the eye 1 during cataract surgery.

Some other approaches improve the visual acuity of presbyopic eyes by extending the depth of focus of the eye by reducing its aperture. Such aperture-reducing designs can deliver notable improvements. There are already products that utilize this design, such as the aperture-decreasing corneal inlays from AcuFocus. These are essentially small, non-transparent discs, with apertures in its middle that act as artificial pupils.

However, such "hard" aperture devices have drawbacks, such as reduced luminescence, and sensitivity to the quality of centration, since an off-center aperture can undermine and degrade visual acuity.

Other systems address presbyopia differently. An analysis of the wave nature of light reveals that the blue spectral component of an image formed by a presbyopic eye on the retina is the blurriest, and the red spectral component of its image is the least blurry. Some IOL manufacturers therefore add a blue filter to their IOLs. Such filters can reduce the blurriest blue component of an image.

However, such blue-filtering IOLs have their own problems, including changes in the color perception of the patient. Therefore, there is still an unmet medical need for new approaches that improve the visual acuity of presbyopic eyes.

SUMMARY

The above-described medical needs are addressed by a color-apodized intraocular lens that includes, a lens center, with a center-transmittance $T_c$ to transmit an incident light; a lens annulus, surrounding the lens center, configured to selectively attenuate the incident light according to a radius- and wavelength-dependent annulus-transmittance $T_a(r,\lambda)$, wherein the annulus-transmittance is less slum the center-transmittance, $T_a(r,\lambda) < T_c$, in a short wavelength spectral range; and haptics, extending from the lens annulus.

Further, a method of making a color-apodized intraocular lens includes creating an intraocular lens mold using a base-polymer, the intraocular lens having a lens center, with a center-transmittance to transmit an incident light; a lens annulus, surrounding the lens center, configured to selectively attenuate the incident light according to a radios and wavelength-dependent annulus-transmittance, wherein the annulus-transmittance is less than the center-transmittance in a short wavelength spectral range; forming Implies, extending from the lens annulus; and applying a stimulus to the intraocular lens mold to form the color-apodized intraocular lens.

DETAILED DESCRIPTION

This document describes embodiments of a color-apodized intra ocular lens (CA-IOL) that provide improvements regarding the above described medical needs.

Figure 1A:
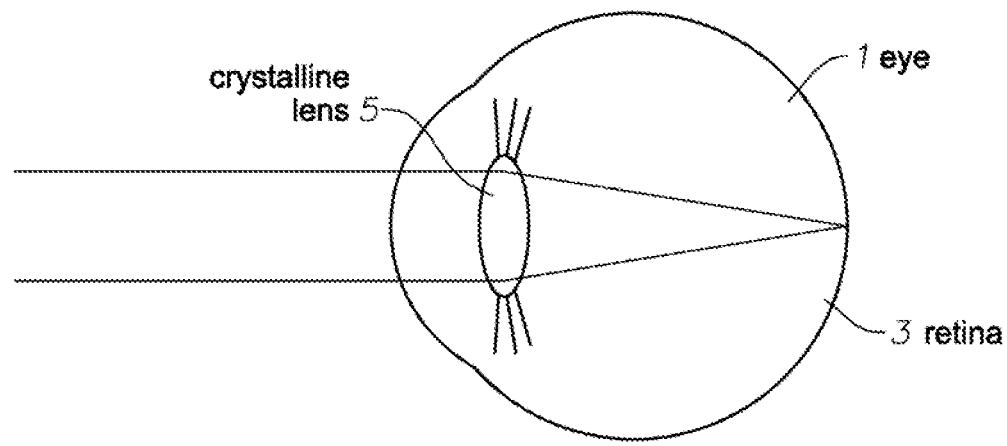
FIGS. 1A-1D illustrates the basics of the problem of presbyopia.
Figure 1B:
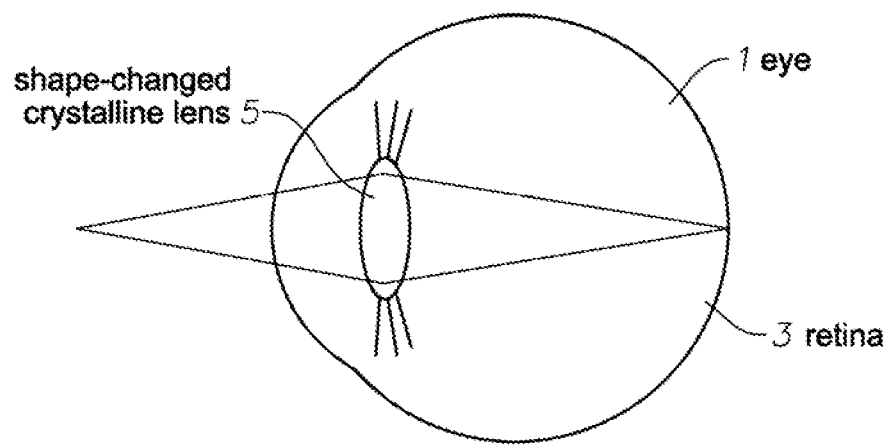
Figure 1C:
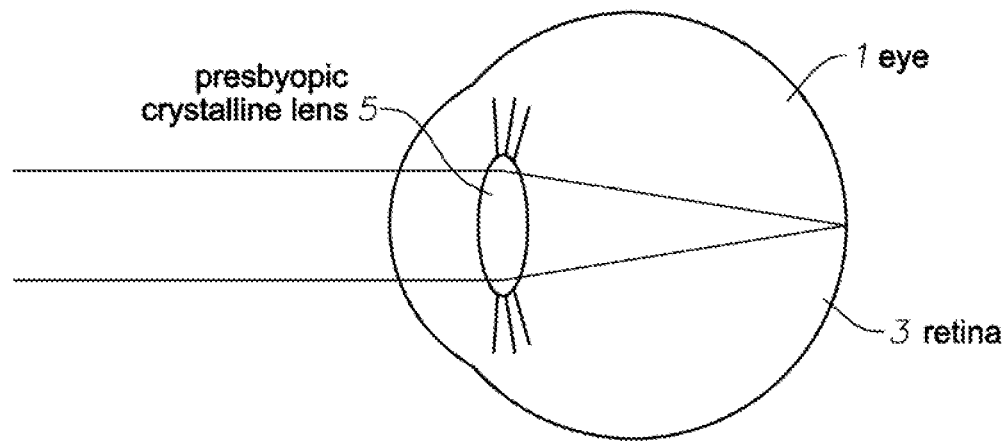
Figure 1D:
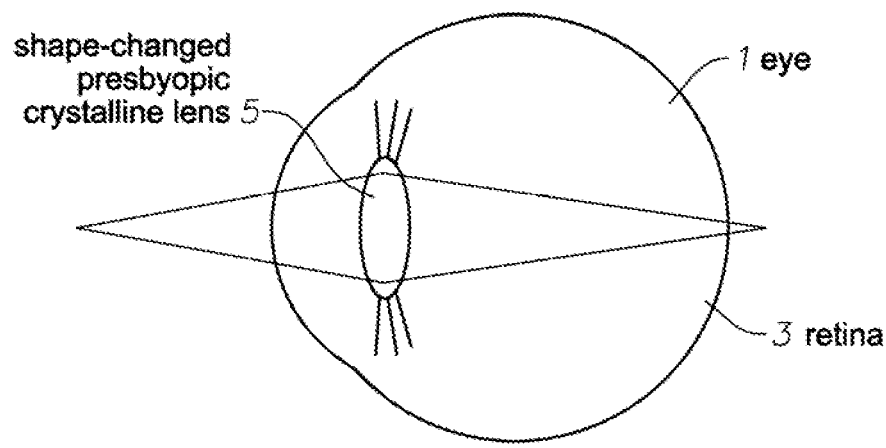
Figure 2:
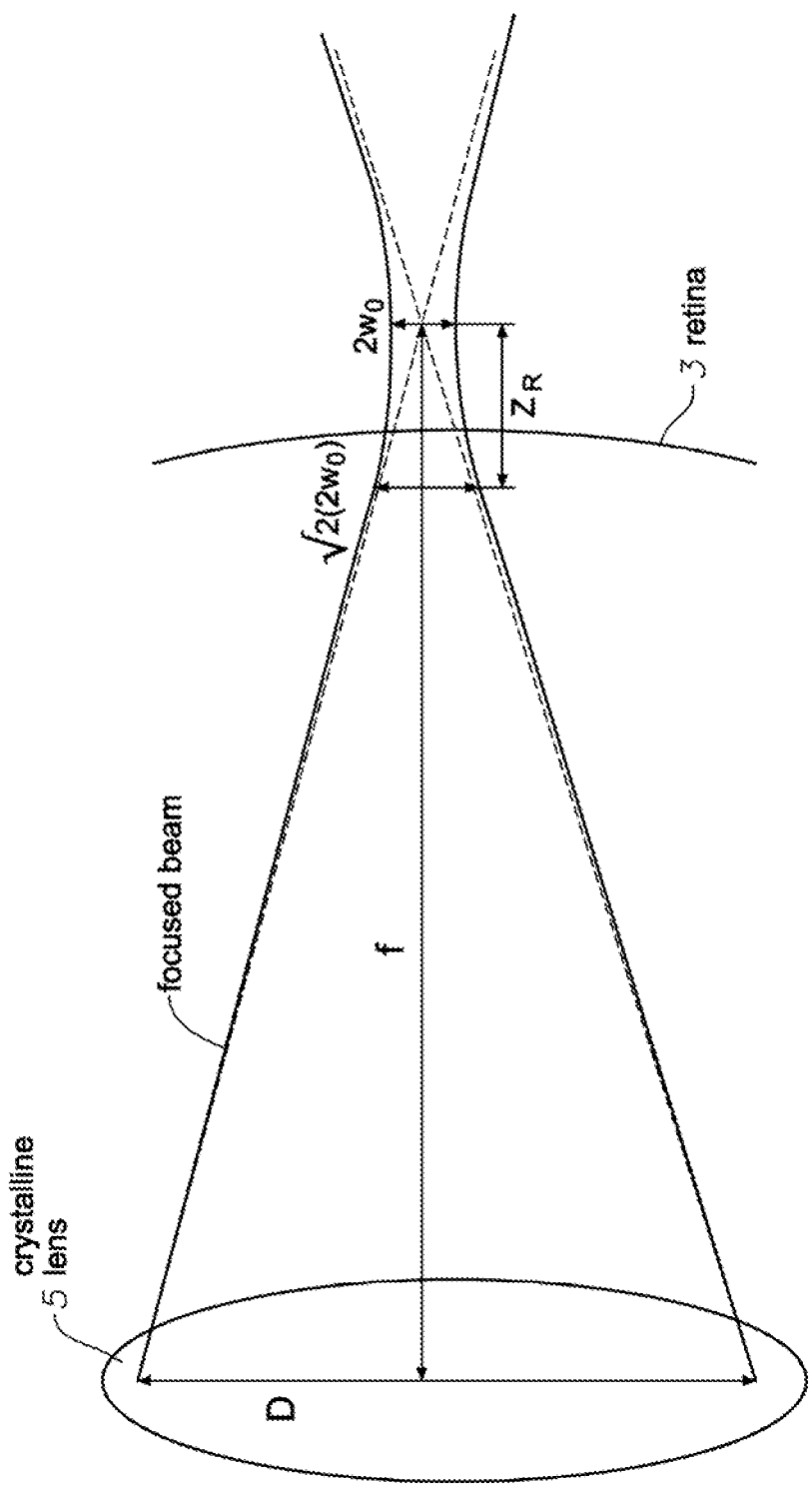
FIG. 2 illustrates the concept of the depth-of-focus of a focused beam.

FIG. 2 illustrates a more detailed analysis of the problem of focusing that builds on the wave nature of light. This analysis reveals that when a beam is focused by a lens of diameter, or aperture, D over a focal distance f, then the wave nature of light, propagating with a wavelength $\lambda$ broadens the beam even at the focal point into a focal spot. The narrowest point of the beam is called the beam waist, having a focal spot diameter of $2w_0$. The beam is broader along the axis in both directions from this focal spot. The distance of the point where the beam diameter is $\sqrt{2}(2w_0)$ from the focal spot itself is called the depth of focus, or Rayleigh length $z_R$. For a lens of diameter, or aperture, D, these quantities are related as:

$$w_0 = \lambda f / D \quad (1)$$

$$z_R = \pi w_0^2 / \lambda = \pi \lambda f^2 / D^2 \quad (2)$$

As visible from FIG. 2, the beam diameter remains close to the minimal beam waist $w_0$ around the focal spot over the x-directional range of $z_R$. Therefore, if an object gets imaged by a presbyopic eye behind the retina, but the image is within a Rayleigh distance $z_R$, the image will still appear clear to the observer. And in reverse, if an object is imaged behind the retina beyond the Rayleigh distance $z_R$, then the image starts to become blurry. This is one of the reasons why $z_R$ is also sometimes referred to as the "depth of focus".

Next, we expand the remarks in the introduction by reviewing designs that improve the visual acuity of presbyopic eyes by extending the depth of focus.

(1) As visible from Eq. (2), the depth of focus $z_R$ can be extended if the lens diameter, or aperture, D is decreased. This is the well-known pinhole effect: the sharpness of the vision can be increased by reducing the aperture. Such systems increase the F#(=f/D) of the lens. Since the depth of focus, or $z_R$, is proportional to the square of the F#, as shown in Eq. (2), such aperture-reducing designs can deliver notable improvements. There are already products that utilize this insight, such as the aperture-decreasing corneal inlay from AcuFocus. This is essentially a small, non-transparent disc, with an aperture that acts as an artificial pupil in its middle. The human pupil in regular outdoor light conditions (with about 85 lumen) has a diameter of about 2.5 mm, so the AcuFocus disc has an outer diameter d(out) larger than 2.5 mm and an inner diameter d(in) that can be selected to be less than 2.5 mm. This d(in) sets the aperture D that determines the depth of focus $z_R$. For D values less than 2.5 mm, an increased visual acuity seems to be achieved with these corneal inlays.

(1a) However, such "hard" aperture devices have drawbacks. The most obvious is the reduced luminescence, since they let through less light. Therefore, in dim light conditions it may he harder to see with these hard apertures.

(1b) A second limitation of such corneal inlays is that the performance of these apertures can be quite sensitive to the quality of centration. An off-center aperture can undermine visual acuity and disorient the patient.

(2) Some systems address presbyopia differently. Visibly, the depth of focus $z_R$ is shorter in the short wavelength blue range of the visible spectrum than in the longer wavelength red range of the spectrum, since $z_R \propto \lambda$. Therefore, if an object is lit with a white light, the blue component of its image by a presbyopic eye on the retina is the blurriest, and the red component of its image is the least blurry. Some IOL manufacturers therefore add a blue filter to their IOLs. Such filters can reduce the blurriest blue component of an image.

Such blue-filtering IOLs have their own problems, however.

(2a) Blue-filtering IOLs add a general yellow hue to the images that is undesirable for patients. They also change the overall color perception.

(2b) Further, it has been proposed that the circadian cycle, related to the human biological clock, is driven by sensing and tracking the central, or peak portion of the solar spectrum, with a wavelength around 520 nm, since this peak light is the strongest in the middle of the day, while the evenings tend to be lit with warmer, yellower, off-peak light. Since some of the blue-filtering IOLs block light even in the central portion, some of them tend to cause a shift or confusion of the circadian cycle, and possibly lead to sleep disorders.

Embodiments of the invention improve the visual acuity of presbyopic eyes, while avoiding the above-mentioned challenges (1a-b) and (2a-b).

Figure 3:
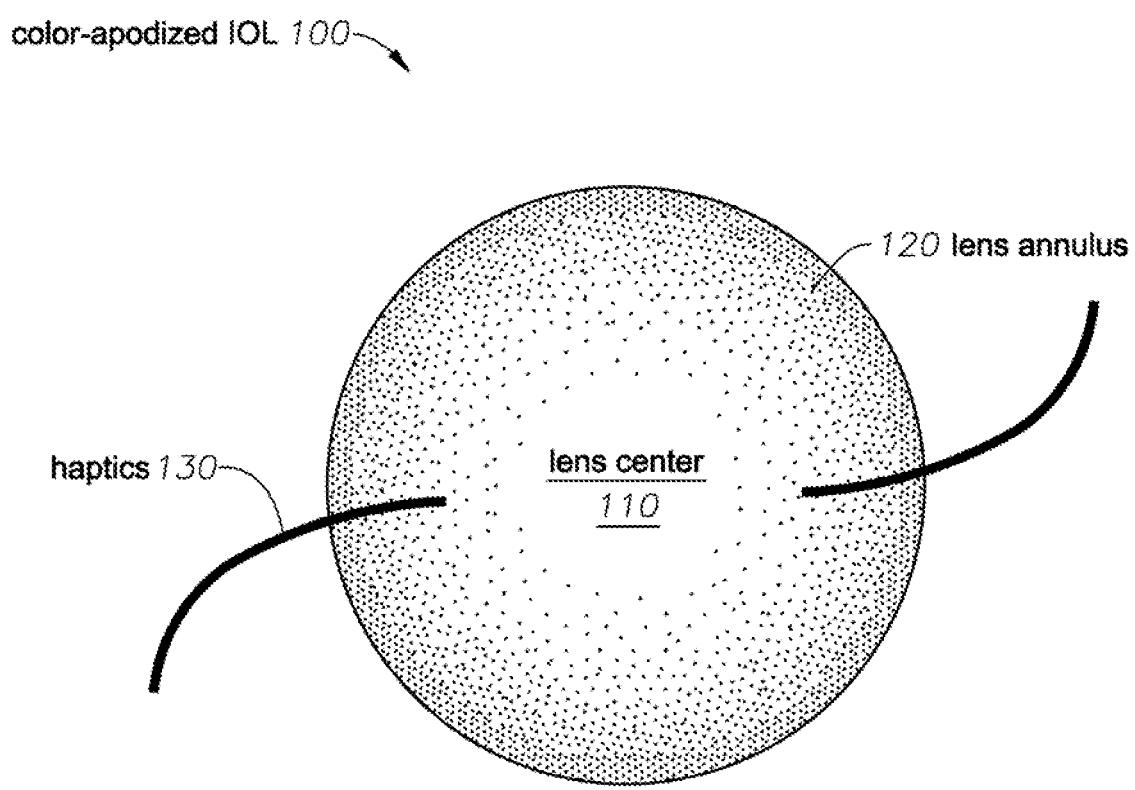
FIG. 3 illustrates an embodiment of a color-apodized IOL 100.

FIG. 3 illustrates an embodiment of a color-apodized intraocular lens 100, or CA-IOL 100 that includes a lens center 110, with a center-transmittance $T_c$ transmit an incident light; a lens annulus 120, surrounding the lens center 110, configured to spectrally attenuate the incident light according to a radius and wavelength-dependent annulus-transmittance $T_a(r,\lambda)$, wherein the annulus-transmittance is less than the center-transmittance, $T_a(r,\lambda) < T_c$ in a short wavelength spectral range.

For brevity, sometimes the annulus-transmittance $T_a(r,\lambda)$ will be referred to as annulus-transmittance $T_a$, or simply as annulus-transmittance 204, and the transmittance across the entire range of the radius r as lens transmittance $T(r,\lambda)$ that equals the center-transmittance $T_c$ in the lens center 110 and the annulus-transmittance $T_a(r,\lambda)$ in the lens annulus 120.

The color-apodized IOL 100, CA-IOL 100 can also include haptics 130 that extend from the lens annulus 120. In some embodiments of the CA-IOL 100, the haptics 130 are separately formed arms, inserted into the CA-IOL 100 during the fabrication process. In other embodiments of the CA-IOL 100, the haptics 130 are formed as part of the cast molding of the CA-IOL 100 itself, in some cases from the same material as the CA-IOL 100 itself.

In some embodiments of the CA-IOL 100, the short wavelength spectral range is characterized by a wavelength range within 350 nm-550 nm. In others, the short wavelength spectral range is characterized by a narrower wavelength range within 400 nm-500 nm, in yet others, within 400-450 nm. In some sense, embodiments of the CA-IOLs 100 have a reduced annulus-transmittance in a blue region of the visible spectrum.

Figure 4A:
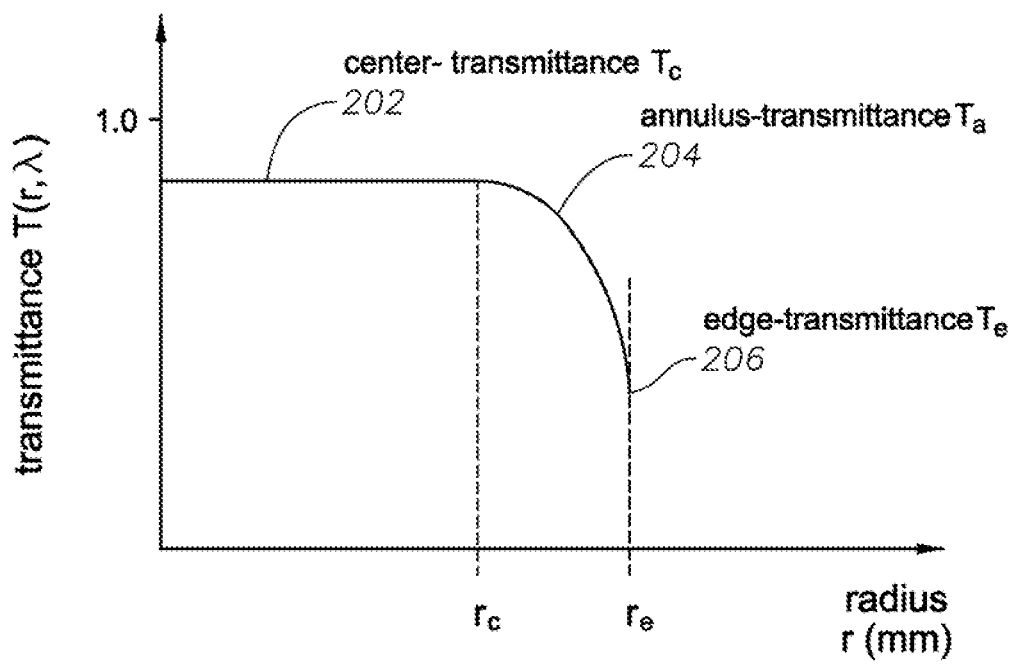
FIGS. 4A-C illiterate the radial dependence of a transmittance of the CA-IOL 100.
Figure 4B:
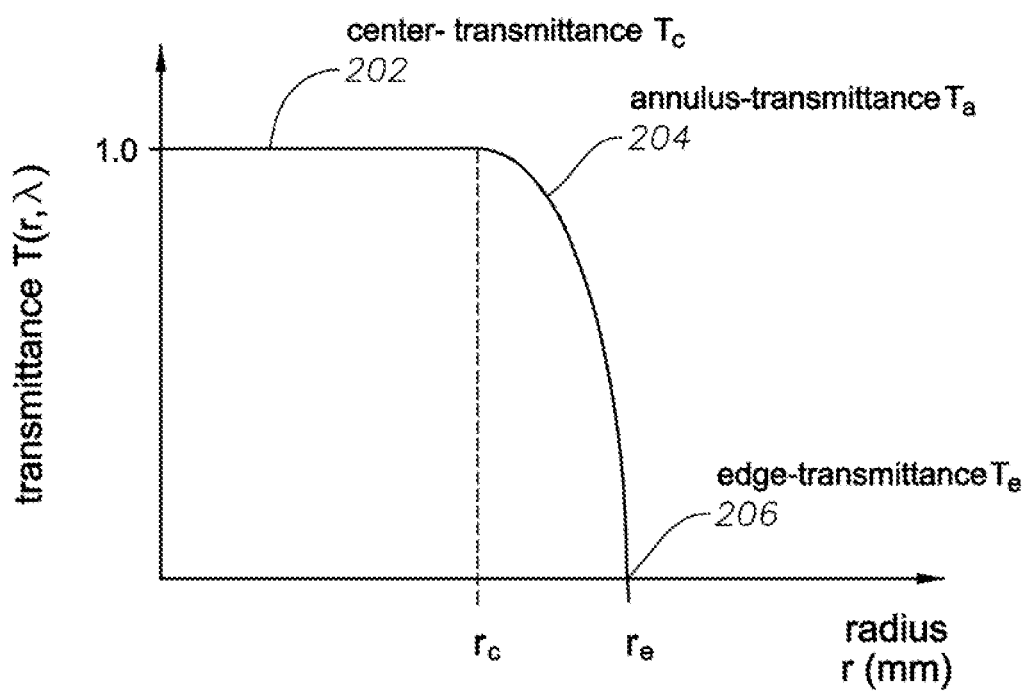
Figure 4C:
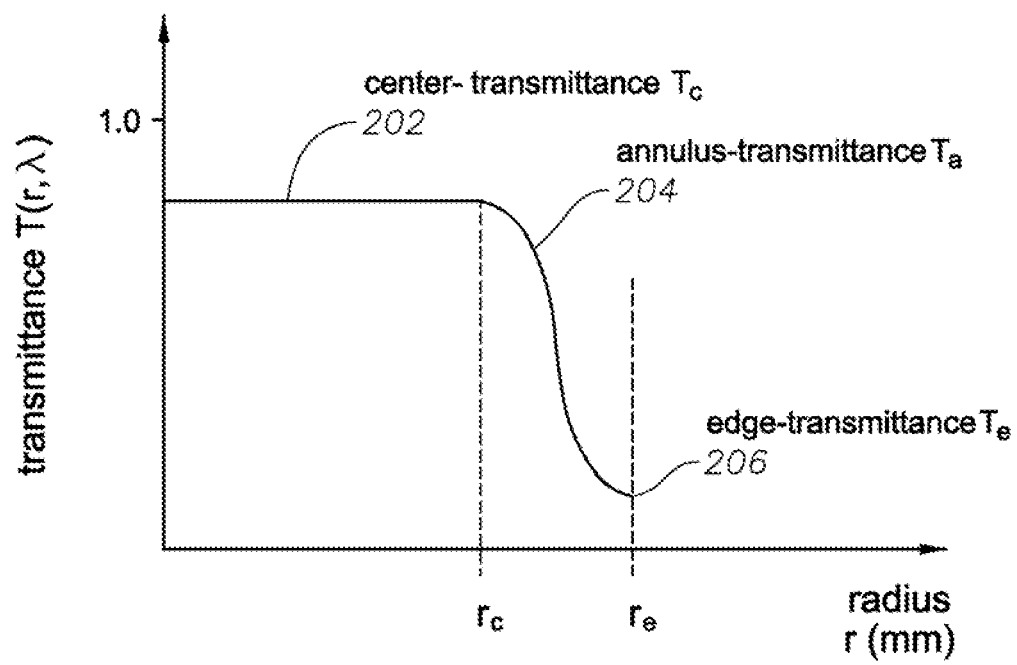

FIGS. 4A-C illustrate that in some embodiments of the CA-IOL 100, the annulus-transmittance $T_a(r,\lambda)$ can gradually decrease with increasing radius for a specific wavelength $\lambda$. As shown, the transmittance $T(r,\lambda)$ of the CA-IOL 100 can start around the center (r=0) with a center-transmittance $T_c$ 202 that characterizes the lens center 110. $T_c$ 202 can be near constant, or can vary to a limited degree with the radius r. In the embodiment of FIG. 4A, the center-transmittance $T_c$ 202 is less than 1, whereas in the embodiment of FIG. 4B $T_c$ 202 is essentially 1. The lens center 110 can extend to a center-radius $r_c$. In some embodiments, $r_c$ can be in the 1.5-2.5 mm range, in others, in the 2.0-2.3 mm range. This center-radius $r_c$ is also the inner radius of the lens annulus 120. An outer radius of the lens annulus 120 can be an edge-radius $r_e$. In embodiments, the edge-radius $r_e$ can be in the 2.3-3.0 mm range, in others, in the 2.5-2.7 mm range. The edge radius $r_e$ can coincide with an outer radius of the CA-IOL 100, or it can be slightly smaller.

FIGS. 4A-C illustrate that the lens annulus 120 can have the annulus-transmittance $T_a(r,\lambda)$, or the annulus-transmittance 204, gradually decreasing from the center-transmittance $T_c$ 202 to an edge transmittance $T_e$ 206. The annulus-transmittance $T_a$ 204 can vary radially according to one of a rectangular window, a B-spline window, a poly-nominal window, a cosine window, a power-of cosine window, an adjustable window, a hybrid window, or any of the known analogues of these windows. Within these windows, the annulus transmittance can take a Hamming form, a Hann form, a Blackmann window, a Gaussian window, or any other of the large number of known analogous forms and windows. In FIGS. 4A-8, the curvature of the annulus-transmittance $T_a$ 204 is steady and does not change sign, whereas in the embodiment of FIG. 4C, it has two curvature regions with opposing signs, separated by an inflection point.

In some embodiments of the CA-IOL 100, the center-transmittance $T_c$ 202 can be in a range of 0.9-1.0, and the annulus-transmittance $T_a$ 204 can decrease from the center-transmittance $T_c$ 202 to an edge transmittance $T_e$ 206 less than 0.7. In some other embodiments, the edge transmittance $T_c$ 206 can be less than 0.3.

Figure 5A:
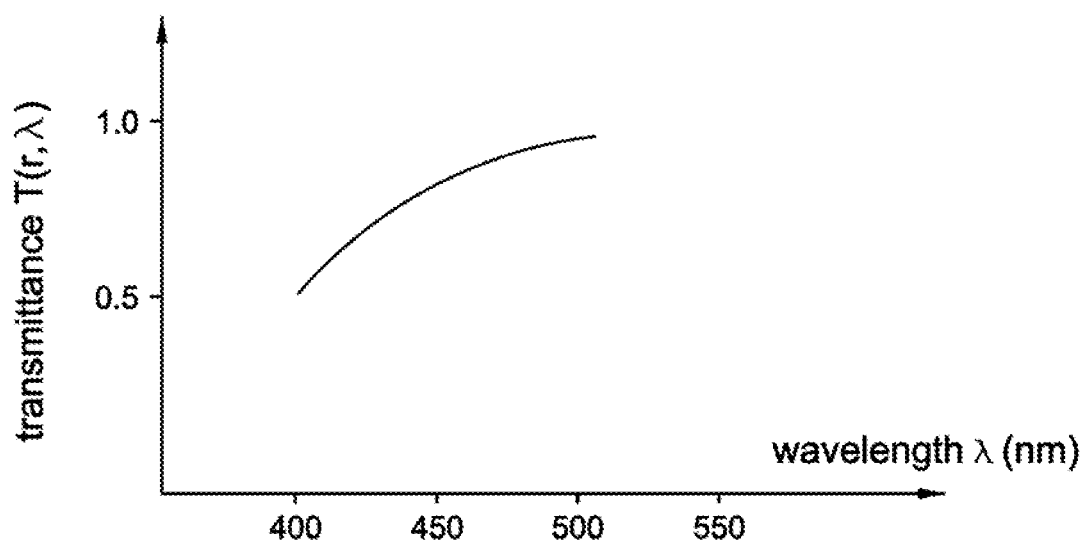
FIGS. 5A-C illustrate the wavelength dependence of the transmittance and the wavelength-dependent aperture $D(\lambda)$.
Figure 5B:
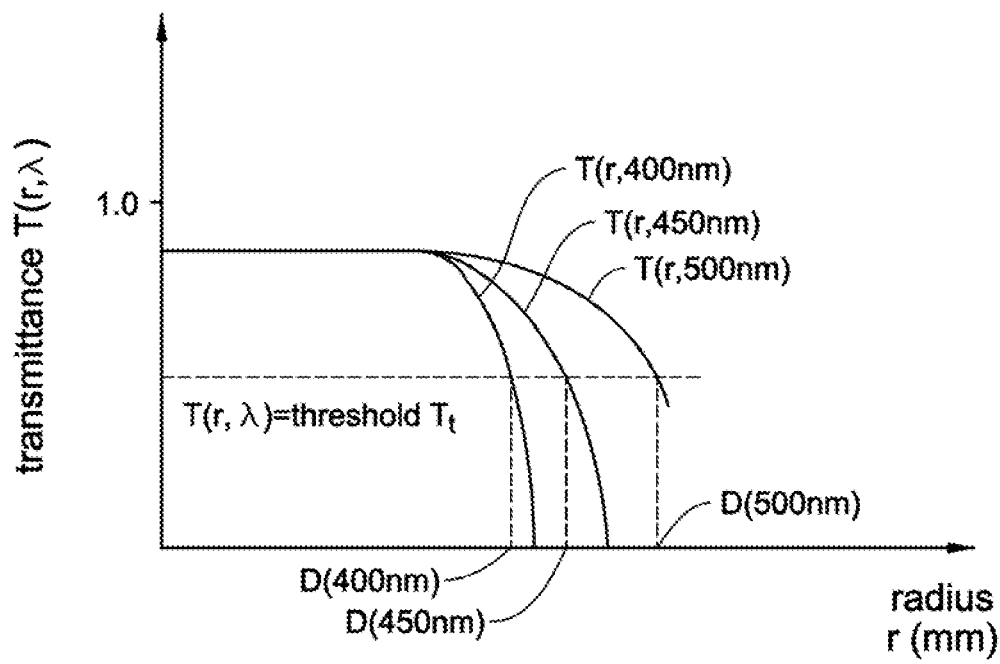
Figure 5C:
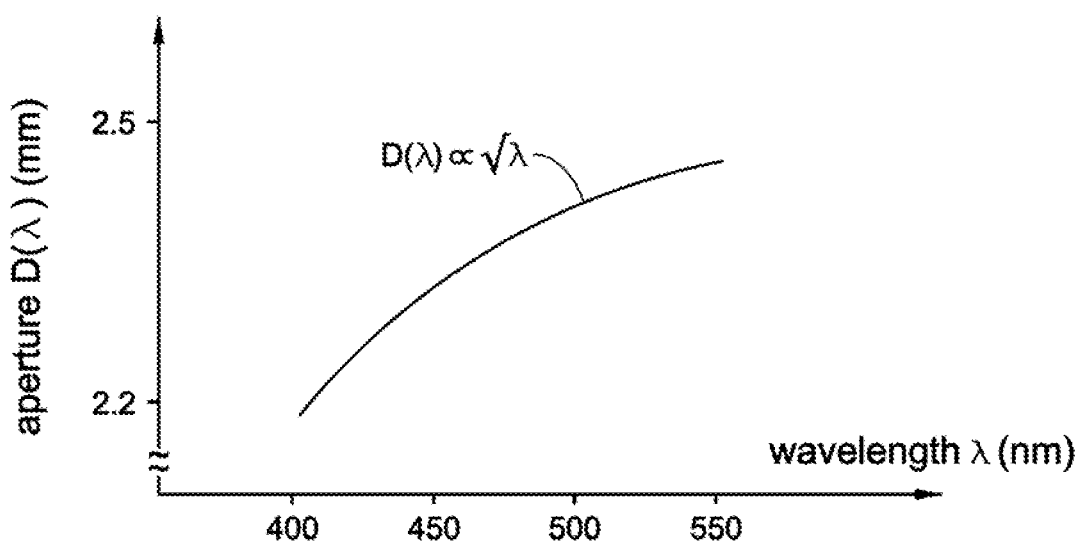

FIGS. 5A-C illustrate that in some CA-IOLs 100, the wavelength dependence of the annulus-transmittance $T_a(r,\lambda)$ can support the definition of a wavelength-dependent aperture $D(\lambda)$ as the radius where the wavelength-dependent annulus-transmittance $T_a(r,\lambda)$ 204 decreases to a threshold value $T_t$:

$$T_a(r=D(\lambda),\lambda)=T_1 \qquad (3)$$

In some detail, FIG. 5A illustrates that in some CA-IOLs 100 the annulus-transmittance $T_a(r,\lambda)$ can increase with increasing wavelength $\lambda$ at a fixed radius r. FIG. 5B illustrates that in such embodiments, the annulus-transmittance 204 can decrease at a slower rate with increasing radius for the longer wavelengths than for shorter wavelengths. Accordingly, the annulus-transmittance $T_a(r,\lambda)$ 204 decreases to the threshold value $T_t$ at a larger radius for longer wavelengths, thus defining a wavelength-dependent aperture $D(\lambda)$ that increases with increasing wavelength $\lambda$. Visibly, the wavelength-dependent aperture $D(\lambda)$, defined by Eq. (3), increases with increasing wavelength $\lambda$: $D(400 \text{ nm}) < D(450 \text{ nm}) < D(500 \text{ nm})$.

Within the CA-IOLs with a wavelength-dependent aperture, there is a class that has an approximately wavelength-independent Rayleigh length $z_R$, or depth, of focus. Using Eq. (2), it is observed that $z_R$ is constant for CA-IOLs 100, which have a constant $\lambda/D(\lambda)^2$ over a range of the wavelengths $\lambda$. In formulae, all CA-IOLs 100 have the same $z_R$ whose wavelength-dependent apertures $D(\lambda)$ satisfy:

$$D(\lambda) = f(\pi\lambda/z_R)^{1/2} \quad (4)$$

FIG. 5C illustrates that for such CA-IOLs, the wavelength-dependent aperture $D(\lambda)$ is proportional to a square root of the wavelength $\lambda$ to provide the wavelength-independent depth of focus, or Rayleigh length $z_R$.

Figure 6A:
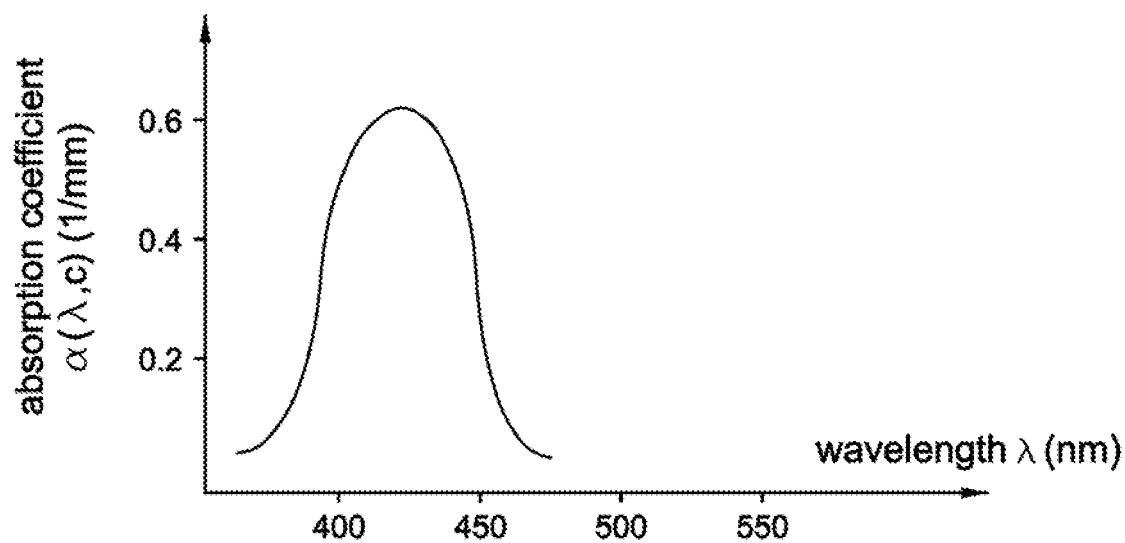
FIGS. 6A-B illustrate the absorption coefficient and the density of an absorber 250.

FIGS. 6A-B and FIGS. 7A-B illustrate that in some embodiments, the wavelength-dependent aperture $D(\lambda)$ can be implemented by the CA-IOL 300 including an absorber 250 with a wavelength-dependent absorption coefficient centered in the short wavelength spectral range. In detail, FIG. 6A illustrates that the absorber 250 can have a wavelength-dependent absorption coefficient $\alpha(\lambda,c)$, which in general can depend both on the wavelength $\lambda$ and on the concentration c of the absorber 250. In the specific shown example, the absorption coefficient $\neq(\lambda,c)$ exhibits a maximum around 425 nm.

Figure 6B:
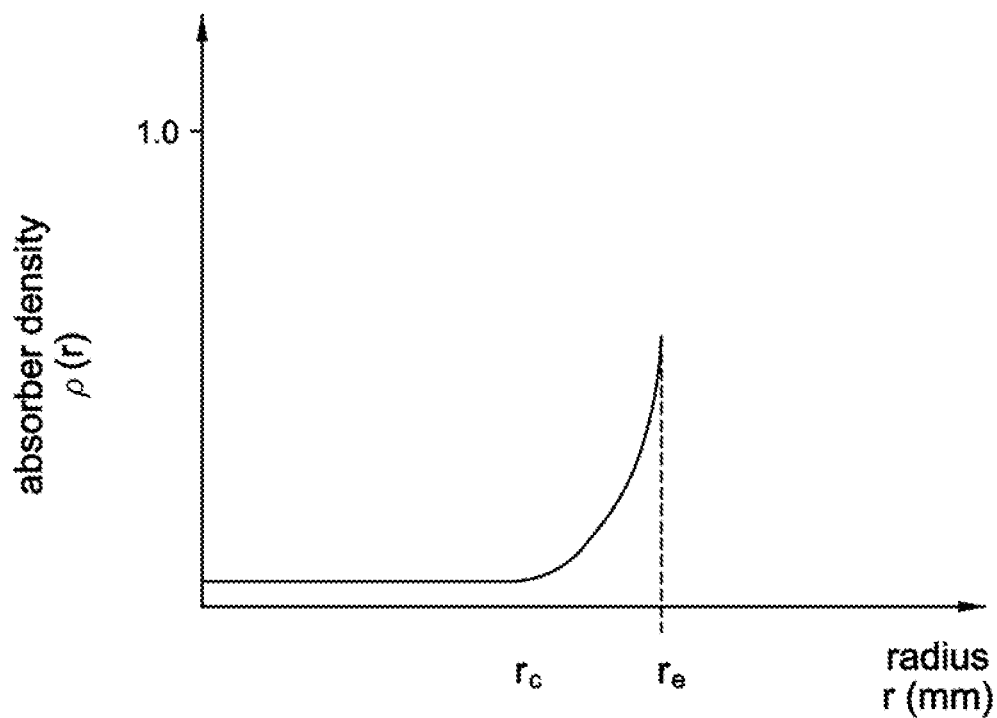

FIG. 6B illustrates the dependence of the density $\rho(r)$ of the absorber 250 on the radius r in some embodiments of the CA-IOL 100. The absorber 250 can have a center-density in the lens center 110, and a higher, radius-dependent annulus-density in the lens annulus 120 that increases with increasing r, thereby causing the annulus-transmittance $T_a$ 204 to be smaller than the center-transmittance $T_c$ 202. The darkening shading of the CA-IOL 100 in FIG. 3 is illustrating such a radially increasing absorber density $\rho(r)$.

Figure 7A:
FIGS. 7A-B illustrate two embodiments of distributing the absorber 250 in the CA-IOL 100.
Figure 7B:

FIG. 7A illustrates that in some embodiments, the absorber 250 can be disposed in a bulk of the CA-IOL 100, and FIG. 7B illustrates that in some embodiments, the absorber 250 can be concentrated in a backlayer 255 of the CA-IOL 100. A gradation in the absorption can be controlled by varying the thickness of the backlayer 255.

In some embodiments, the CA-IOL 100 can be a light-adjustable lens as described e.g. in the commonly owned U.S. Pat. No. 6,450,642, to J. M. Jethmalani et al., entitled: "Lenses capable of post-fabrication power modification", hereby incorporated in its entirety by reference. The absorber 250 can be a wide variety of absorbers as described in the '642 incorporated patent. In some embodiments, the absorber 250 can be activable by radiation after an implantation of the color-apodized, light adjustable intraocular lens 100 into an eye 1. The activable absorber 250 can be a caged absorber, capable of getting released from a molecular cage by a first irradiation. In some embodiments, the activable absorber can be made less absorptive with a second irradiation. In such embodiments, the density of the activated absorber 250 can be both increased and decreased by applying appropriate radiation even after the implantation of the CA IOL 100 into the eye.

In other embodiments of the CA-IOL 100, the absorber 250 can be activable by a two-photon process. Such embodiments of the CA-IOL 100 can be protected more readily from un-intended activation.

In both the light-adjustable lenses and non-light-adjustable lenses, the absorber 250 can be a blue absorber that includes benzotriazoles, benzophenones, azobenzene, or their compounds. A class of blue absorbers can include at least one blue absorber linked to a short polymer chain. The short polymer chain can be compatible with the polymers which form the CA-IOL 100. For example, for CA-IOLs 100 formed from silica containing polymers, the short chain can also be a silica based polymer; for polyacrylate based CA IOLs 100, the short chain can be an acrylate based polymer.

A wide variety of further blue absorbers are known in the arts. Many of them are described, and their relative merits discussed, in the commonly owned U.S. Pat. No. 9,119,710 to R. H. Grubbs and S. Chang, entitled "Adjustable optical elements with enhanced ultraviolet protection" ("'710 patent"), hereby incorporated in its entirety by reference. The '710 patent describes, among others, benzotriazoles with groups X, $R^1$ and $R^2$ attached to them. For example, the X group, attached to the benzene ring of the benzotriazole, can be selected from H, monovalent hydrocarbon radicals and monovalent substituted hydrocarbon radicals preferably containing 1 to about 8 carbon atoms, hydroxyl radicals, amino radicals, carboxyl radicals, alkoxy radicals and substituted alkoxy radicals, preferably containing 1 to 6 carbon atoms and halogen radicals. Any of the ultraviolet absorbers described in the '710 patent can be usefully employed in embodiments of the CA IOLs 100, in some embodiments with appropriate modification to shift their maximum absorption wavelength to the 400-500 nm range, in some embodiments to the 400-450 nm range.

Next, it is reviewed how embodiments of the CA-IOL 100 provide solutions for the above problems (1a-b) and (2a-b) of other designs.

(1a) Embodiments of the CA-IOL 100 do not have a hard, opaque aperture, as they reduce the effective aperture only in the short-wavelength, "blue" spectral region. Accordingly, the CA-IOLs reduce the luminescence much less than hard, opaque aperture designs.

(1b) Embodiments of the CA-IOL 100 can he centered well inside the capsule of the eye and thus avoid the problems arising from centration. This is especially true for the CA-IOLs, where the absorber is activated after the insertion of the CA-IOL. In these systems, the surgeon can wait until the CA-IOL 100 settles into its final position, possibly weeks after the cataract surgery, and apply a radiation only afterwards to activate the absorber according to a pattern that centers the lens annulus 120 and the wavelength-dependent aperture with high precision.

(2a) CA-IOLs do not add a general yellow hue to the image across the entire IOL either, as they employ a blue-reducing aperture only in the lens annulus 120. As such, they modify the overall color perception of the patients to a much lesser degree than the overall blue-blocking IOLs.

(2b) As shown in FIGS. 5A and 6A, some embodiments of the CA-IOL 100 have an absorber 250 that absorbs only light with wavelengths less than 520 nm. Such CA-IOLs 100 avoid causing a shift, or a confusion of the circadian cycle, and thus avoid causing sleep disorders.

Figure 8:
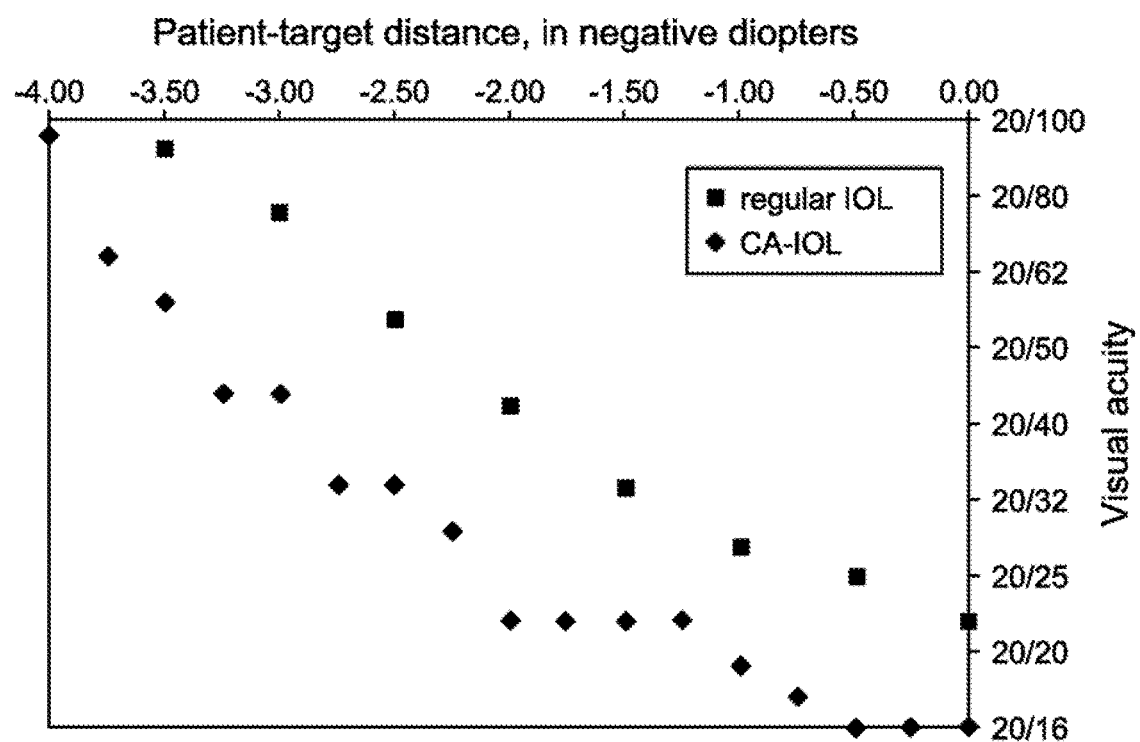
FIG. 8 illustrates the gains achieved in visual acuity by patients using the principles of the CA-IOLs.

FIG. 8 illustrates the results of a study that was carried out to analyze the visual acuity improvements brought about by simulated embodiments of the CA-IOL 100 relative to corresponding non-color-apodized IOLs.

The horizontal, x axis shows the patient-target distance, expressed in negative diopters D, the inverse of the distance. E.g. a 2 meter patient-target distance is shown as −1;2m= −0.5 D. The vertical y axis shows the measured visual acuity (VA), expressed in the usual 20/N Snellen form. [A 20/N visual acuity expresses that a patient has to stand 20 feet from the target to visually resolve two closely spaced points that a person with a standard healthy vision can resolve from N feet.] When this 20/N ratio is viewed as a fraction and evaluated to yield a number, this is called the Decimal Visual Acuity, or Decimal VA. E.g. the Decimal VA of a 20/40 Snellen VA is 20:40=0.5. An equivalent representation of visual acuity is in terms of the MAR, or the "minimum angle of resolution". These two representations are connected as: Decimal VA=1/MAR. The well-known, FDA standard ETDRS lines of the opthamalic tables each represent a 0.1 step in the logarithm of MAR, or log(MAR), where the 20/20 vision with a decimal VA of 1, and thus log(MAR)=0 was taken as the reference. The Snellen VA values, corresponding to these 0.1 log(MAR) steps, and thus to the lines of the ophthalmic tables are:

TABLE 1

| | Log(MAR) | | | | | | | |
|---|---|---|---|---|---|---|---|---|
| | 0.0 | 0.1 | 0.2 | 0.3 | 0.4 | 0.5 | 0.6 | 0.7 |
| Snellen VA | 20/20 | 20/25 | 20/32 | 20/40 | 20/50 | 20/62 | 20/80 | 20/100 |

The ticks on the vertically axis in FIG. 8 represent these 0.1 steps of log(MAR) and corresponding Snellen VA values. As such, each tick represents a line of the FDA standard ETDRS ophthalmic table.

FIG. 8 illustrates the results of the above mentioned comparative study of the visual acuity of patients with standard IOLs and those with simulated embodiments of CA-IOLs 100. Visibly, patients with CA-IOLs experienced a significant improvement of their visual acuity by about 2 lines at all target distances relative to patients with regular IOLs.

Figure 9:
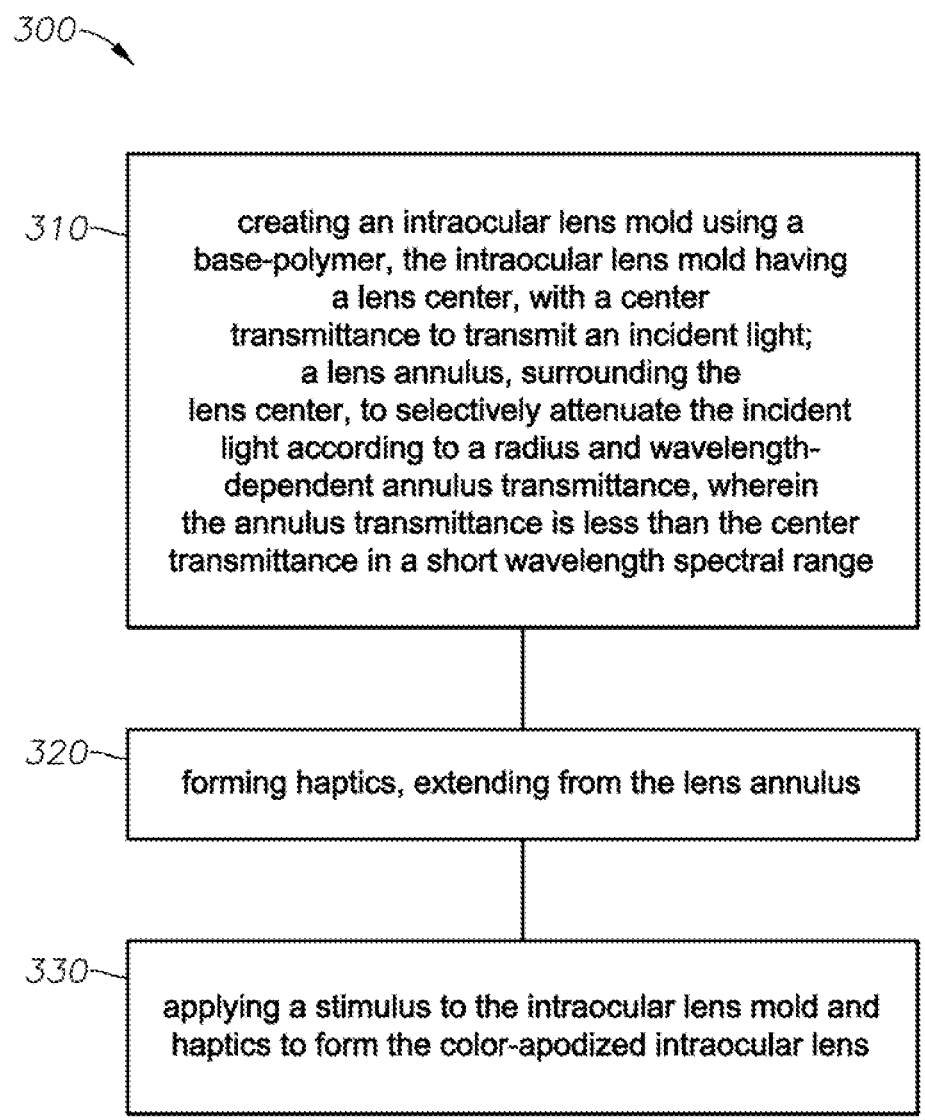
FIG. 9 illustrates a method 300 to fabricate CA-IOLs.

FIG. 9 illustrates a method 300 of making a color-apodized intraocular lens 100, the method 300 comprising the following steps.

310—creating an intraocular lens mold using a base-polymer, the intraocular lens having
a lens center 110, with a center-transmittance to transmit an incident light;
a lens annulus 120, surrounding the lens center 110, configured to selectively attenuate the incident light according to a radius and wavelength-dependent annulus-transmittance, wherein
the annulus-transmittance is less than the center-transmittance in a short wavelength spectral range;

320—forming haptics 130, extending from the lens annulus 120; and

330—applying a stimulus to the intraocular lens mold and haptics to form the color-apodized intraocular lens 100.

In some embodiments, the short wavelength spectral range can be characterized by a wavelength range within 400 nm-500 nm. In some embodiments, the annulus-transmittance gradually decreases with the radius increasing.

In some embodiments, the creating 310 can include introducing an absorber 250 into the base polymer with a wavelength-dependent absorption coefficient centered in the short wavelength spectral range.

The introducing can include introducing the absorber with a center-density in the lens center 110; and introducing the absorber with a higher annulus-density in the lens annulus 120, thereby causing the annulus-transmittance 204 to be smaller than the center-transmittance 202.

In some embodiments, the color-apodized intraocular lens 100 can be a light-adjustable lens, and the method 300 can include activating the absorber 250 by applying a radiation after an implantation of the color-apodized intraocular lens 100 into an eye.

The activating can include activating a caged absorber, capable of being released from a molecular cage by a first irradiation. In some embodiments, the absorber may be made less absorptive by applying a second irradiation of a different wavelength.

In some other embodiments, the activating can include activating the absorber by a two-photon process.

In some embodiments, the forming 320 can include forming the haptics from the same lens mold, integrated with the creating step 310; or forming the haptics separately and inserting them into the intraocular lens CA-IOL 100.

In some embodiments, the applying a stimulus 330 can include applying a heat stimulus or a light stimulus to the intraocular lens mold and haptics to form the color-apodized intraocular lens 100.

While this document, contains many specifics, details and numerical ranges, these should not be construed as limitations of the scope of the invention and of the claims, but, rather, as descriptions of features specific to particular embodiments of the invention. Certain features that are described in this document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised front the combination, and the claimed combination may be directed to another subcombination or a variation of a subcombinations.

The invention claimed is:

1. A color-apodized intraocular lens, comprising:
a lens center, with a center-transmittance $T_c$ to transmit an incident light;
a lens annulus, surrounding the lens center, configured to selectively attenuate the incident light according to a radius- and wavelength-dependent annulus-transmittance $T_a(r,\lambda)$, wherein
the annulus-transmittance is less than the center-transmittance, $T_a(r,\lambda) < T_c$, in a short wavelength spectral range; and
haptics, extending from the lens annulus, wherein
the annulus-transmittance gradually decreases with the radius increasing; and
the annulus-transmittance varies radially according to one of a rectangular window, a B-spline window, a polynominal window, a cosine window, a power-of cosine window, an adjustable window, a hybrid window, a Hamming form, a Hann form, a Blackman window, and a Gaussian window.

2. The color-apodized intraocular lens of claim 1, wherein:

the short wavelength spectral range is characterized by a wavelength range within 350 nm -550 nm.

3. The color-apodized intraocular lens of claim 1, wherein:
the short wavelength spectral range is characterized by a wavelength range within 400 nm -500 nm.

4. The color-apodized intraocular lens of claim 1, wherein:
the center-transmittance $T_e$ is in a range of 0.9-1.0; and
the annulus-transmittance $T_a(r,\lambda)$ decreases from the center-transmittance $T_e$ to an edge transmittance $T_e$ less than 0.7 with increasing radius.

5. The color-apodized intraocular lens of claim 4, wherein:
the edge transmittance $T_e$ is less than 0.3.

6. The color-apodized intraocular lens of claim 1, wherein:
the color-apodized intraocular lens has a wavelength-dependent aperture $D(\lambda)$, defined as the radius where the wavelength-dependent annulus-transmittance $T_a(r,\lambda)$ decreases to a threshold value $T_t$, $T_a(r=D(\lambda),\lambda)=T_t$; and
the wavelength-dependent aperture $D(\lambda)$ varies proportional to a square root of the wavelength.

7. The color-apodized intraocular lens of claim 1, comprising:
an absorber, with a wavelength-dependent absorption coefficient centered in the short wavelength spectral range.

8. The color-apodized intraocular lens of claim 7, wherein:
the absorber has a center-density in the lens center, and a radius-dependent annulus-density in the lens annulus that increases with increasing radius, thereby causing the annulus-transmittance to be smaller than the center-transmittance.

9. The color-apodized intraocular lens of claim 7, wherein:
the absorber is disposed in one of a bulk of the color-apodized intraocular lens, and in a backlayer of the color-apodized intraocular lens.

10. The color-apodized intraocular lens of claim 7, wherein:
the color-apodized intraocular lens is a light-adjustable lens.

11. The color-apodized intraocular lens of claim 10, wherein:
the absorber is activable by radiation after an implantation of the color-apodized intraocular lens into an eye.

12. The color-apodized intraocular lens of claim 10, wherein:
the absorber is a caged absorber, capable of
getting released from a molecular cage by a first irradiation; and
becoming less absorptive upon a second irradiation.

13. The color-apodized intraocular lens of claim 10, wherein:
the absorber is activable by a two-photon process.

14. The color-apodized intraocular lens of claim 7, the absorber comprising at least one of:
a benzotriazole-based compound and a benzophenone-based compound.

* * * * *